United States Patent [19]

Wermuth et al.

[11] 3,996,231
[45] Dec. 7, 1976

[54] 1-QUINOLINYL-PYRAZOLIDINE DERIVATIVES

[75] Inventors: Camille Georges Wermuth, Strasbourg; Jean Choay, Paris, both of France

[73] Assignee: Choay S.A., Paris, France

[22] Filed: July 11, 1974

[21] Appl. No.: 487,536

[30] Foreign Application Priority Data

July 13, 1973 France .................. 73.25857

[52] U.S. Cl. .............. 260/288 CE; 260/283 R; 260/287 F; 260/288 R; 260/289 R; 424/258
[51] Int. Cl.[2] .................. C07D 401/04
[58] Field of Search ............ 260/288 CE, 287 F

[56] References Cited
OTHER PUBLICATIONS

Weissberger et al., Chem. Abstr., vol. 39, col. 933, 1945.
Yasuyuki et al., Chem. Abstr., vol. 56, col. 3451b, 1962.
Golankiewicz, Chem. Abstr., vol. 60, col. 4107b, 1961.
Itai et al., Chem. Abstr., vol. 55, 27338c, (1961).

*Primary Examiner*—Nicholas S. Rizzo
*Assistant Examiner*—Mary C. Vaughn
*Attorney, Agent, or Firm*—Weiser, Stapler & Spivak

[57] ABSTRACT

The derivatives have the general formula

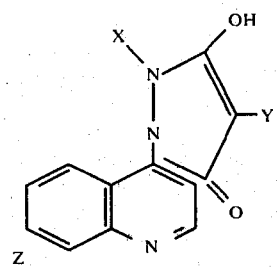

in which X is a hydrogen atom or a methyl, phenyl or benzyl group; Y is a carbon chain comprising 2 to 6 carbon atoms, saturated or unsaturated, unsubstituted or substituted by alkyl, alkoxyl or halogen groups, said chain including if necessary, instead and in place of an aliphatic link, a carbonyl or alcohol group; Z is constituted by a hydrogen atom or defines at least an alkyl, alkoxyl or halogen group fixed at any position of the quinolinyl nucleus. They have high anti-inflammatory and analgesic activities.

20 Claims, No Drawings

1-QUINOLINYL-PYRAZOLIDINE DERIVATIVES

The invention relates to new derivatives of pyrazolidine, to a method for manufacturing these derivatives and to medicaments containing them.

The new derivatives according to the invention are characterised by the general formula

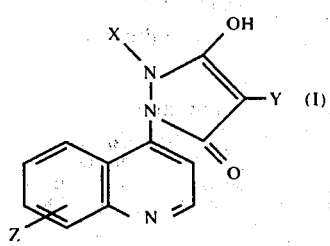

in which X is a hydrogen atom or a methyl, phenyl or benzyl group;

Y is a carbon chain comprising 2 to 6 carbon atoms, saturated or unsaturated, unsubstituted or substituted by alkyl, alkoxy or halogen groups, this chain comprising if necessary, instead and in place of an aliphatic link a carbonyl or alcohol group;

Z is constitituted by a hydrogen atom or defines at least one alkyl, alkoxy or halogen or a trifluoromethyl group fixed at any position of the quinolinyl nucleus.

In a preferred group of substances selected from the above-mentioned family, the Y group is an aliphatic chain containing from 2 to 6 carbon atoms.

A still narrower preferred group is that defined by the abovesaid formula I in which X has the above-indicated significance, Y is a butyl group and Z is a hydrogen or halogen atom or trifluoromethyl or methoxy group.

There may also be mentioned a group in which X has the above-indicated significance, Y is an aliphatic chain containing from 2 to 6 carbon atoms, one of the hydrocarbon groups inside this aliphatic chain being, if necessary, replaced by a carbonyl group and Z is a hydrogen atom or a chlorine atom at the 7' position or a trifluoromethyl group at the 8' position of the quinolinyl group.

The method of manufacturing derivatives of the type concerned is characterised in that the quinoline derivative of the formula

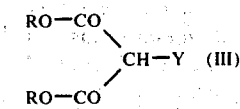

in which Q is a halogen group and Z has the above-indicated significance is reacted with a hydrazine of the formula H₂N-NHX in which X has the above-indicated significance, the derivative of 4-hydrazino quinoline obtained is reacted with an n-alkylmalonate of the formula $$\begin{array}{c} RO-CO \\ \phantom{RO-}\diagdown \\ \phantom{RO-CO\diagdown}CH-Y \quad (III) \\ \phantom{RO-}\diagup \\ RO-CO \end{array}$$

in which R is an alkyl group and Y has the above-indicated significance in the presence of an alkaline condensing agent such as an alkali alcoholate, for example sodium ethylate, the product of the reaction is taken up in acid medium and the product which is insoluble in aqueous medium is recovered.

These reactions are preferably effected in the midst of solvents, the solvent used in the 4-hydrazino quinoline reaction with n-alkylmalonate being removed by evaporation, if necessary under reduced pressure, prior to placing the solid residue obtained in contact with an aqueous acid solution.

One of the substances of this family which has a particular interest is constituted by 1-(7'-chloro 4-quinolinyl) 3,5-dioxo 4-n-butyl pyrazolidine of the formula

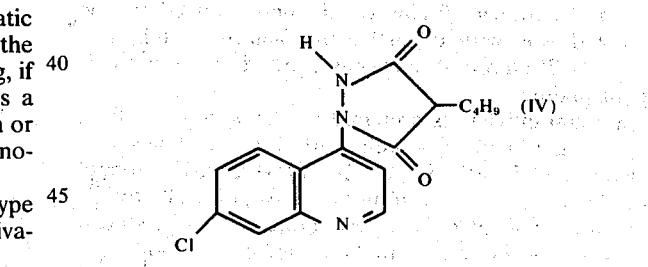

This substance can for example be manufactured by resorting to the following reactions:

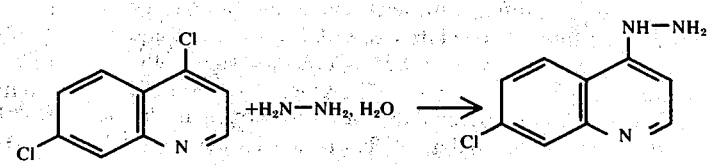

then:

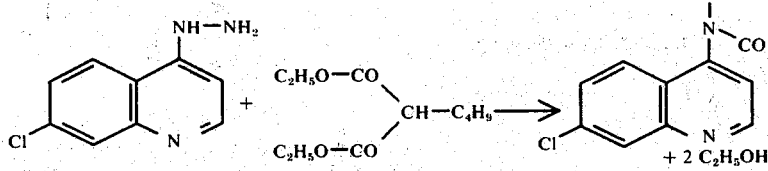

The products according to the invention are characterised by pharmacological properties which render them valuable medicaments, for example anti-inflammatories. Pharmacological testing has in fact established in substances of the type concerned activities, for example anti-inflammatory and analgesic, particularly high in the case of 1-(7'-chloro 4-quinolinyl) 3,5-dioxo 4-n-butyl pyrazolidine.

Other features of the invention will appear also in the course of the following description of examples of substances according to the invention, of their methods of preparation and their pharmacological properties. 1. Preparation of 1-(7'-chloro 4-quinolinyl) 3,5-dioxo 4-n-butyl pyrazolidine a. 4-hydrazino 7-chloro quinoline The following mixture is heated under reflux by means of an oil bath for eight hours under a current of nitrogen:

40 g of 4,7-dichloro quinoline
40 g of hydrazine hydrate
150 ml of absolute alcohol.

On cooling yellow crystals are obtained which are filtered, washed with water, then with alcohol.

They are dried in an oven at 80° and the crystals are protected from light and air.

Yield: 24 g, namely 60% of theoretical yield.

The 4-hydrazino 7-chloro quinoline obtained may be reacted as is, without further purification, as follows.

b. 1-(7'-chloro 4-quinolinyl) 3,5-dioxo 4-n-butyl-pyrazolidine

Sodium ethylate is prepared by the action of 4.09 g (0.178 g-atoms) of sodium with 100 ml of absolute alcohol. 33.5 g (0.155 mole) of ethyl n-butylmalonate is added and the mixture is stirred magnetically for 15 minutes. The alcohol is evaporated under reduced pressure. 90 ml of dimethylformamide is added to the residue, a current of nitrogen is bubbled through and 32.9 g (0.17 mole) of 4-hydrazino 7-chloro quinoline is added. It is heated by means of an oil bath to 150° for 12 hours under nitrogen the alcohol formed distilling therefrom.

The dimethylformamide is then evaporated under reduced pressure. The residue is taken up with water. It is filtered. The aqueous phase is washed with ethyl acetate. It is acidified with acetic acid and the orange precipitate filtered. The latter is washed with water and it is recrystallised twice in 95% alcohol, stopping the heating on boiling. 13.5 g of 1-(7'-chloro 4'-quinolinyl) 3,5-dioxo 4-n-butyl pyrazolidine are thus obtained, this product having the analytical characteristics and properties indicated below.

M.P. (Mettler) = 164.5° C
Molecular weight = 317.77

| M.P. (Mettler) | = | 164.5° C |
|---|---|---|
| Molecular weight | = | 317.77 |
| Emperical formula: | | $C_{16}H_{16}O_2N_3Cl$ |

-continued

| Analysis | : | C | H | N |
|---|---|---|---|---|
| Calc. % | : | 60.47 | 5.08 | 13.22 |
| Found % | : | 60.67 | 5.06 | 13.17 |

It is in the form of fine crystals, insoluble in water, soluble in alcohol and in solutions of potassium or of sodium carbonate.

When it is dissolved in a mixture containing 40% of methanol, 55% of ethyl acetate and 5% of diethylamine, it gives, in thin layer chromatography

| - a rather long stain of rf | = | 0.57 |
|---|---|---|
| - a weak stain of rf invisible under UV | = | 0.77 yellow, but |
| - a trace of rf | = | 0.84. |

Under similar conditions, and using corresponding starting compounds, the products identified below are prepared:

1-(4'-quinolinyl) 3,5-dioxo 4-ethyl pyrazolidine
1-(4'-quinolinyl) 3,5-dioxo 4-n-butyl pyrazolidine
1-(4'-quinolinyl) 3,5-dioxo 4-isobutyl pyrazolidine
1-(7'-chloro 4'-quinolinyl) 3,5-dioxo 4-ethyl pyrazolidine
1-(7'-chloro 4'-quinolinyl) 3,5-dioxo 4-n-propyl pyrazolidine
1-(8'-trifluoromethyl 4'-quinolinyl) 3,5-dioxo 4-ethyl pyrazolidine
1-(8'-trifluoromethyl 4'-quinolinyl) 3,5-dioxo 4-n-propyl pyrazolidine
1-(8'-trifluoromethyl 4'-quinolinyl) 3,5-dioxo 4-n-butyl pyrazolidine
1-(8'-trifluoromethyl 4'-quinolinyl) 3,5-dioxo 4-n-pentyl pyrazolidine
1-(4'-quinolinyl) 2-methyl 3,5-dioxo 4-ethyl pyrazolidine
1-(4'-quinolinyl) 2-methyl 3,5-dioxo 4-n-butyl pyrazolidine
1-(7'-chloro 4'-quinolinyl) 2-methyl 3,5-dioxo 4-n-butyl pyrazolidine
1-(7'-chloro 4'-quinolinyl) 2-phenyl 3,5-dioxo 4-n-butyl pyrazolidine
1-(7'-chloro 4'-quinolinyl) 2-benzyl 3,5-dioxo 4-n-butyl pyrazolidine
1-(7'-chloro 4'-quinolinyl) 3,5-dioxo 4-n-crotonyl pyrazolidine The family of substances according to the invention has analgesic activity and, especially considerable anti-inflammatory activity, as is witnessed by pharmacological tests effected on a preferred substance and particularly representative of this family, namely 1-(7'-chloro 4'-quinolinyl) 3,5-dioxo 4-n-butyl pyrazolidine, which tests are described below.

I - Determination of the anti-inflammatory activity

This is carried out by means of a number of tests enabling the action of the substance according to the invention on various inflammatory processes to be studied.

a. Ovalbumin oedema and carragenin oedema in the rat

"Ovalbumin oedema" is caused by the injection of 0.2 ml of ovalbumin into the plantar surface of the right rear foot of the rat.

The increase, due to oedema, of the size of the foot, is measured in this test by means of the Giono and Chevillard plethysmometer. The measurements are done every 10 minutes for 90 minutes.

The "carragenin oedema" is caused by the injection of 0.5 ml of a 1% aqueous solution of carragenin in the plantar pad of the rat's foot. This oedema, of inflammatory type, develops in about 8 hours. It is at its maximum intensity at the fourth hour after the injection of the carragein.

The rats are sacrificed 4 hours after the injection of the carragenin. The two rear feet are cut off at the same level and weight.

The magnitude of the inflammatory phenomenon is estimated by the weight of the foot which has undergone the injection. The local inflammation is manifested by an increase in weight of this foot with respect to the weight of the opposite healthy foot.

The action of the substance according to the invention is manifested, in treated rats, by oedemas of lesser magnitude than in the control rats. In each of the tests whose results are shown in Tables I and II below, the action of the substances tested is expressed by the average percentage in reduction of oedema observed in the treated animals, relative to the average amount of oedema in the control series, which comprise, 7 rats each time. The extreme percentages which were observable in each series is also shown in this Table.

The substances to be tested were administered by the oral route, at doses shown in the first columns of the Tables. 1-(7'-chloro 4'-quinolinyl) 3,5-dioxo 4-n-butyl pyrazolidine was administered in suspension in gum tragacanth at the doses indicated in the Tables below.

TABLE I

| | Ovalbumin Oedema | |
|---|---|---|
| Dose administered | Average of the results (reduction in oedema, in %) | Standard Deviations |
| 50 mg/kg | − 45 % | 5.6 |
| 25 mg/kg | − 38 % | 6.2 |
| 12.5 mg/kg | − 15 % | 4.3 |

TABLE II

| | Carragenin Oedema | |
|---|---|---|
| Dose administered | Average of the results (reduction in oedema, in %) | Standard Deviations |
| 50 mg/kg | − 51 % | 5.1 |
| 25 mg/kg | − 48 % | 5.4 |
| 12.5 mg/kg | − 38 % | 6.1 | b. Kaolin arthritis

The injection of 0.05 ml of a sterile 10% suspension of kaolin into the metatarsal flexor sheath of the rear foot of the rat causes, the first time, an oedematous reaction. An inflammatory arthritis is then generated.

The early oedematous reaction appears in the first hour and reaches its maximum between the fourth and sixth hours. It is this effect which is of interest. The estimation of the volume of the foot enables the action of substances on the oedematous reaction to be studied. The measurements are done every hour by means of the Giono and Chevillard plethysmometer.

As in the preceding case, there was observed in the treated animals a reduction in oedema, which reduction is expressed in Table III below and as % with respect to oedema caused under the same conditions in rats of a series of 7 control animals, as in the preceding case.

TABLE III

| | Kaolin Arthritis | |
|---|---|---|
| Dose administered | Average of the results (reduction in oedema, in %) | Standard Deviations |
| 50 mg/kg | − 54 % | 4.8 |
| 25 mg/kg | − 48 % | 4.5 |
| 12.5 mg/kg | − 32 % | 5.4 |

All the preceding experiments hence establish a real effect of the substance according to the invention with respect to the oedematous phases of inflammation.

c. Test of granuloma produced by a foreign body (pad of cotton)

This test enables the effect of the substance to be tested on the tissular phase of inflammation to be estimated.

Under the skin of rats, pads of cotton for dental dressings, 50 mg in weight, previously sterilised in the autoclave, are implanted. The implantation is carried out under the skin of the back, in the right and left lumbar regions.

The introduction of these foreign bodies results in the formation of granuloma formed of a very characteristic inflammatory tissue, whose weight gives a measurement of the degree of inflammation.

The anti-inflammatory activity of the substance tested is manifested in this test by the reduction in the average weight of the granuloma in the treated animals (compared with that obtained in a series of 7 control animals) 5 days after the implantation of the cotton pad. The results of these experiments are reproduced in Table IV below.

TABLE IV

| | Granuloma by a foreign body | |
|---|---|---|
| Dose administered | Average of the results (reduction in average weight of the granuloma, in %) | Standard Deviations |
| 50 mg/kg | − 50 % (8 days of treatment) | 5.4 |
| 25 mg/kg | − 47 % | 6.2 |
| 12.5 mg/kg | − 42 % | 5.1 | d. Experimental pleurisy in the rat

The injection of terebenthine essence (0.1 ml) into the bottom of the diaphragmatic sack of the rat causes in the hours which follow a vascular parietal reaction which leads to the formation of an inflammatory type pleurisy.

The average volume of the pleural exudate (taken up after opening the thoracic cage of the previously sacrificed animals) increases gradually in control animals to reach 6 to 7 ml towards the sixth hour, this volume remaining constant to the forty-eighth hour. The exudate is accompanied by the diapedesis of the formed elements of the blood and by the increase in the mobile cells of the conjunctive tissue. Five days after the injection of the irritant agent, the cellular phase gives place to a tissular reaction which leads to the building of dense granulation tissue and to the production of adhesions between the lungs and the thoracic wall.

The action of an anti-inflammatory substance is manifested by a reduction in the volume of the pleural exudate measured for example 6 hours after the injection of the irritant agent and by a reduction in the intensity of the later tissular reaction.

The substances according to the invention, for example 1-(7'-chloro 4'-quinolinyl) 3,5-dioxo 4-n-butyl pyrazolidine testify also in this test two a particularly high anti-inflammatory reaction, as emerges from the comparative results of Table V below, obtained with 1-(7'-chloro 4'-quinolinyl) 3,5-dioxo 4-n-butyl pyrazolidine, and non-steroid substances with anti-inflammatory activity and known under the names or connotations: Phenylbutazone, Indomethacine, Flufenamic acid, Mefanamic acid, Niflumic acid, Clofezone.

Experiments in Wistar rats of 200 g divided into batches in the following manner were carried out:

1 control batch of 15 animals 2 batches of 45 animals (batches 1 and 2) divided into sub-groups of 15 animals treated with the doses indicated in Table V batch of 60 animals (batch 3) also divided into sub-groups, each of them comprising 20 animals which have been treated with the doses indicated in Table V 6 batches of 15 animals, respectively treated with anti-inflammatory substances for comparison identified above.

The substances to be tested were administered by mouth 30 minutes before the injection of the irritant substance. The doses of these known anti-inflammatories correspond to their normal experimental doses. The results indicated in the Table V correspond to the reductions expressed as % of the average volumes of pleural exudate taken up 6 hours after the irritant injection and observed in the treated animals relative to the average volumes measured in the controls.

The injection of 0.5 ml of Freund adjuvant (product sold by the Difco Company) into the plantar pad of the rear foot of a rat of 90 days, causes a chronic polyarthritis.

This injection causes an inflammation first localised in the injected foot, then generalised. The blocking of the articulations appears between the 10th and the 20th days.

In a series of rats thus treated there are selected, 10 days after the injection of the Freund adjuvant, 50 rats having complete blockage of the articulations. These rats are divided into a group of 25 rats (control rats) and into another group, of which the rats are then treated with 1-(7'-chloro 4'-quinolinyl) 3,5-dioxo 4-n-butyl pyrazolidine at the dose of 50 mg/kg per day.

After 5, 10 and 15 days of treatment there is observed in the group of treated animals an at least partial deblocking of the articulations in at least 25, 50 and 65% of the animals respectively. No articulation deblocking is observed in the control animals.

This particularly severe test, hence establishes in a particularly distinct manner the good curative effect of the substance according to the invention.

It hence results from the foregoing that the substances according to the invention have a real antiinflammatory activity extending over all of the phenomena studied, whatever the mechanism, whether it be vasculooedematous, cellular or tissular.

II - Determination of the analgesic activity

I. Randall and Selitto test

This test (Arch. int. Pharmacodyn. 1957, CXI, 409–419) is based on the principle that inflammation increases sensitivity to pain, especially on pressure, and that analgesics raise the threshold of this sensitivity.

Inflammation is achieved by the injection, under the plantar aponeural of one of the rear feet, of 0.1 ml of a 20% aqueous suspension of brewers yeast. The pain is caused by a force supplied to the plantar surface and gradually increased by 16 g/second. The pain threshold is estimated by the force necessary and sufficient to trigger a characteristic withdrawal reaction of the foot.

The sensitivity to pain of the inflamed foot reaches a plateau 4 hours after the injection of the brewers yeast

TABLE V

| Substance | Doses | Batch No.1 | Standard Deviation | Batch No. 2 | Standard Deviation | Batch No. 3 | Standard Deviation |
|---|---|---|---|---|---|---|---|
| 1-(7'-chloro 4' quinolinyl) 3,5-dioxo 4-n-butyl pyrazolidine | 50 mg/kg | −45% | 5.4 | −55% | 5.9 | −45% | 6.1 |
| | 25 mg/kg | −35% | 6.1 | −38% | 5.1 | −28% | 5.4 |
| | 12.5 mg/kg | −24% | 5.0 | −23% | 6.2 | −18% | 5.1 |
| Phenylbutazone | 100 mg/kg | −49% | 5.4 | | | | |
| Indomethacine | 5 mg/kg | −33% | 6.2 | | | | |
| Ac. flufenamic | 25 mg/kg | −32% | 6.1 | | | | |
| Ac. Mefenamic | 25 mg/kg | −30% | 5.1 | | | | |
| Ac. niflumic | 50 mg/kg | −30% | 5.2 | | | | |
| Clofezone | 50 mg/kg | −37% | 5.1 | | | | |

These tests establish the high activity of the substance according to the invention, which can be considered as greater than the most effective of the comparative substances if one takes into consideration not the crude doses which are shown in the Table, but the Therapeutic Indexes of the substances concerned (ratio of the active doses 50 ($AD_{50}$) and of the lethal doses 50 $LD_{50}$)). It emerges in fact from this description that the $LD_{50}$ of the substance according to the invention is particularly high. e. Arthritis by Freund adjuvant and then remains stable up to the sixth. The pain threshold of the inflamed foot is, in the control rats of 140 grams, reached at pressures of 50 to 60 g, whilst it is situated around 160 g for the intact foot.

The effect of the substance according to the invention is expressed, when administered by mouth, in series of 15 rats at doses indicated in the Table below, by the percentage increase of the average threshold of pain with respect to that measured in rats of a control series of 15 animals.

TABLE VI

Randall and Selitto Test

| Dose administered | Average results (increase in threshold, in %) | Standard Deviations |
|---|---|---|
| 50 mg/kg | + 29 % (15 rats/dose) | 6.1 |
| 25 mg/kg | + 23 % | 5.7 |
| 12.5 mg/kg | + 21 % | 4.5 |

This test hence establishes, a notable activity of the tested substance with respect to pain due to inflammation.

2. Test of contortions by acetic acid

The injection of acetic acid by the intraperitoneal route in the mouse causes contortions or stretchings in the animal.

A solution of 6 parts per 1000 of acetic acid in 10% gum water is used.

The technic consists of injecting 0.1 ml of this solution per 10 g of weight of mouse. After 5 min, the number of stretchings of the animal is counted. The administration of an analgesic substance leads to a reduction of the number of these contorsions.

The product to be tested is force fed 30 mn before the injecton of the acetic acid solution.

The average stretchings of the animals in each of the tested groups is compared with the average number of stretchings of a control group (20 animals per group) and the percentage of reduction in the average number of the stretchings is calculated. The results obtained with 1-(7'-chloro 4'-quinolinyl) 3,5-dioxo 4-n-butyl pyrazolidine are shown in table VII below.

Table VII

Cramps with acetic acid

| Dose administered | Average results (reduction in the number of contortions as %) | Standard Deviations |
|---|---|---|
| 100 mg/kg | − 65% (20 mice/dose) | 5.2 |
| 50 mg/kg | − 51% | 6.8 |
| 25 mg/kg | − 46% | 4.8 |
| 12.5 mg/kg | − 28% | 5.3 |

3. Caroll and Lim test

This test (Arch. Int. Pharmacodyn., 1960, CXXV, 383–403) enables the study of the effect of analgesics on the transmission of painful stimuli, by means of electrodes placed on the tail of the rat and connected to a "stimulator" constituted by a source adapted to supply an alternating current of 60 Hz frequency at increasing voltages. The three voltages (thresholds $S_1$, $S_2$, $S_3$) at which there are successively obtained:

Threshold $S_1$ : characteristic retraction movement of the tail

Threshold $S_2$ : a cry

Threshold $S_3$ : a cry which continues after interrupting the stimulation.

The analgesic substances administered to a group of 15 rats have the effect of increasing the values of these thresholds. This is what have been observed with the substance according to the invention, administered by mouth at the dose of 50 mg/kg. The average increases, expressed as % with respect to the average corresponding thresholds observed in 15 animals of a control series, are indicated in Table VIII below.

Table VIII

Caroll and Lim Test

| Time of measurement after administration of the product | Threshold | Average results | Standard Deviations |
|---|---|---|---|
| 30 minutes | $S_1$ | 0 | — |
| | $S_2$ | + 37% | 6.8 |
| | $S_3$ | + 29% | 6.7 |
| 1 hour | $S_1$ | 0 | — |
| | $S_2$ | + 50% | 5.8 |
| | $S_3$ | + 29% | 5.6 |
| 1½ hour | $S_1$ | 0 | — |
| | $S_2$ | + 50% | 6.8 |
| | $S_3$ | + 40% | 5.4 |
| 2 hours | $S_1$ | 0 | — |
| | $S_2$ | + 50% | 6.4 |
| | $S_3$ | + 35% | 6.1 |

The remarkable anti-inflammatory activity of the derivatives according to the invention, and more particularly of 1-(7'-chloro 4'-quinolinyl) 3,5-dioxo 4-n-butyl pyrazolidine is hence supplemented by a distinct analgesic action, as is witnessed by the results of the analgesia tests which have just been described.

III - Non-toxicity of the substances according to the invention

The substances according to the invention, and more particularly 1-(7'-chloro 4'-quinolinyl) 3,5-dioxo 4-n-butyl pyrazolidine, are characterized by a remarkable short term lack of toxicity. $LD_{50}$ were determined in the mouse and the rat. The substance was administered to the animals by the oral route in a single dose. The behaviour of the animals was observed during the six days which followed. The statistical calculations were done by the method of Miller L. C. Tainter M. L. (Proc. Soc. Exp. Biol. Med., 1944 57 261/264). The results obtained were as follows:

In the mouse (20 mice per dose) :

| Dose administered by mouse | Average results |
|---|---|
| 200 mg/kg | no death |
| 500 mg/kg | no death |
| 1 g/kg | 16% mortality |
| 2 g/kg | 50% mortality |
| 4 g/kg | 100% mortality |

In the rat (10 rats per dose) :

| Dose administered by rat | Average results |
|---|---|
| 200 mg/kg | no death |
| 500 mg/kg | no death |
| 1 g/kg | no death |
| 2 g/kg | no death |
| 4 g/kg | 5% mortality |

It is concluded that the $LD_{50}$ in the mouse (by mouth) is of the order of 2 g/kg, the $LD_{50}$ in the rat (by mouth) is higher than 4 g/kg.

If it is taken into account that the $AD_{50}$ (activedose 50) of this substance, as shown by the abovementioned tests, is of the order of 50 mg/kg in all the animals, it will be observed that there is available, with the substance according to the invention, an active principle for an analgesic and anti-inflammatory medicament, having an excellent therapeutic index, notably higher than that of phenylbutazone. The $AD_{50}$ of thhe latter (determined under similar conditions) is only in fact of the order of 100 mg/kg, whilst its $LD_{50}$ in the rat and the mouse are much lower than the above-indicated values.

The remarkable anti-inflammatory properties of the substances according to the invention hence provide particularly useful active principles for the constitution of medicaments. The invention relates also to the salts of these substances, for example those which the latter form with physiologically acceptable acids, and consequently the medicaments constituted with the latter salts.

It follows from the nature of the pharmacologic properties these substances have, that their use as a medicament can be contemplated for the treatment of any inflammatory type of disorder. They are particularly indicated for the treatment of inflammatory and painful conditions, both acute and chronic, of rhumatoid arthritis, inflammatory crisis and pains of arthrosis and discopathies.

The daily doses recommended are of the order of 50 to 500, preferably 100 to 300 mg/day in man. These values are only of course by way of being indicative. They can be exceeded if the nature of the disorders to be treated requires it.

The medicaments can be offered in the form of pharmaceutical compositions intended for oral administration, for example in the form of solid compositions in which the derivatives according to the invention are associated with pharmaceutically acceptable solid excipients. These compositions can be in any conventional form, such as pils, tablets, gelules, powders, granules, etc.

The medicaments according to the invention may also be administered by the rectal route, the derivatives according to the invention being then associated with any conventional excipients for suppositories, such as polyglycols, cocoa butter, etc.

The derivatives according to the invention may also constitute the active principle of pomades, in which they are associated with conventional pomade excipients. The pomades obtained are then suitable for the treatment of dermal or epidermal disorders of inflammatory nature.

The derivatives according to the invention may also be administered by the parenteral route, for example in the form of suspensions in a pharmaceutically acceptable, sterile, liquid vehicle, for example physiological serum, said derivatives having previously undergone sufficient grinding for them to be in the form of particles of a sufficiently small granulometry for the suspension to be effectively injected.

As is self evident and as emerges already from the foregoing, the invention is in no way limited to those of its types of application and embodiments, which have been more especially envisaged; but encompasses, on the contrary, all modifications.

We claim:
1. A compound of the formula

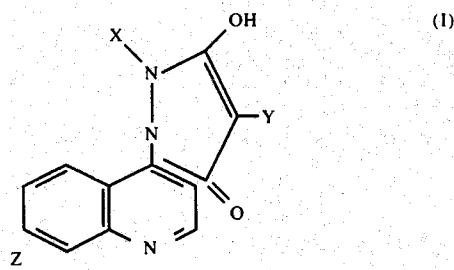

in which X is hydrogen or methyl, phenyl or benzyl;
Y is alkyl, alkenyl or alkyl-, alkenyl- having a -C:OH group and of 2 to 6 carbon atoms;
Z is hydrogen, trifluoromethyl, methoxy or halogen fixed at any position of the quinolinyl nucleus.

2. A compound of claim 1, wherein Y is alkyl.
3. The compounds of the formula

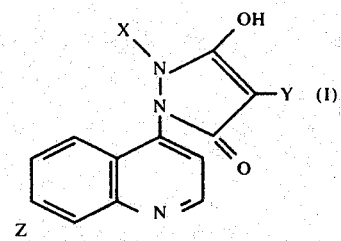

in which X is hydrogen or methyl, phenyl or benzyl;
Y is alkyl or alkenyl of 2 to 4 carbon atoms or said radical having a carbonyl or an hydroxyl group and
Z is hydrogen, trifluoromethyl, methoxy or a halogen group fixed at any position of the quinolinyl nucleus.

4. A compound of claim 3, wherein Y is alkyl and Z is chloro.
5. A compound of claim 3, wherein Y is alkenyl and Z is chloro.
6. 1-(7'-chloro-4'-quinolinyl) 3,5-dioxo 4-n-butyl-pyrazolidine.
7. The method of manufacturing a compound defined in claim 3, which comprises the step of reacting without causing substitution on the alpha-position respective the nitrogen on the quinoline, the quinoline of the formula $$\text{(II)}$$

in which Z is defined in claim 1, with a hydrazine of the formula $H_2N\text{-}NHX$ in which X has the above indicated significance, reacting the 4-hydrazino quinoline obtained with an n-alkylmalonate of the formula $$\begin{array}{c} RO-CO \\ \phantom{RO-CO}\diagdown \\ \phantom{RO-CO}\phantom{xx}CH-Y \quad \text{(III)} \\ \phantom{RO-CO}\diagup \\ RO-CO \end{array}$$

in which Q is a hologen, R is an alky group of 2 to 6 carbon atoms or crotonyl and Y is defined in claim 26 in the presence of an alkali alcoholate, taking up the reaction product in an acid medium and recovering the product of formula (I) which is insoluble in aqueous medium.

8. A compound of the formula of claim 1 wherein X is hydrogen, methyl, phenyl or benzyl, Y is crotonyl, Z is hydrogen or is chlorine in the 7'-position or trifluoromethyl in the 8'-position of the quinolinyl group.

9. The compound of claim 8 wherein X is hydrogen, Y is crotonyl and Z is 7'-chloro.

10. The compounds of claim 3 in which Y has a carbonyl group.

11. The compounds of claim 3 in which Y has an alcohol group.

12. A compound of claim 3 wherein Y is butyl.

13. The compound of claim 5 wherein Y is crotonyl.

14. A compound of claim 3 wherein Z is chloro.

15. A compound of claim 3 wherein the chloro is the 70'-position.

16. A compound of claim 3 wherein Z is trifluoromethyl in the 8'-position.

17. The process of claim 7 in which the reaction with the n-alkyl malonate is carried out in the presence of dimethylformamide.

18. The method of manufacturing a compound of formula I of claim 1 wherein the substituents are there defined which comprises the steps of reacting by bringing together at a reactive temperature, a 4-hydrazino quinoline of the formula

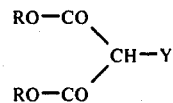

with an n-alkylmalonate of the formula

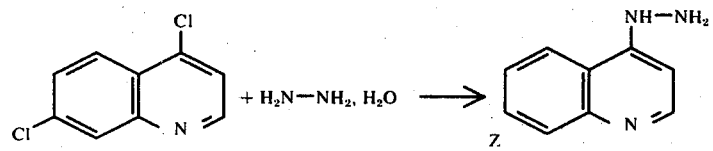

wherein Y is alkenyl, alkyl or carbonyl- or hydroxyl-substituted alkyl or alkenyl, said group having 2 to 6 carbon atoms, in the presence of the alkali alcoholate and separating the compound of formula I, the compound being soluble in aqueous medium.

19. The method of claim 18 wherein the reaction is carried out in the presence of dimethyformamide.

20. The method of claim 18 wherein X is hydrogen, Y is alkyl, and Z is chloro.

* * * * *